United States Patent
Holmes et al.

(10) Patent No.: US 7,375,248 B2
(45) Date of Patent: May 20, 2008

(54) INHIBITORS OF MATRIX METALLOPROTEINASE

(75) Inventors: Ian Holmes, Stevenage (GB); Stephen Paul Watson, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 10/561,055

(22) PCT Filed: Jun. 16, 2004

(86) PCT No.: PCT/EP2004/006553

§ 371 (c)(1),
(2), (4) Date: Dec. 16, 2005

(87) PCT Pub. No.: WO2004/113279

PCT Pub. Date: Dec. 29, 2004

(65) Prior Publication Data

US 2006/0142385 A1    Jun. 29, 2006

(30) Foreign Application Priority Data

Jun. 20, 2003  (GB) ................. 031 44 888

(51) Int. Cl.
  C07C 315/00 (2006.01)
  C07C 229/00 (2006.01)
  A01N 37/34 (2006.01)
  A01N 37/12 (2006.01)

(52) U.S. Cl. ............ 562/430; 514/521; 514/562; 548/410

(58) Field of Classification Search ........ 562/430, 562/450; 514/411; 548/472
See application file for complete search history.

(56) References Cited

U.S. PATENT DOCUMENTS

| | | | |
|---|---|---|---|
| 5,710,171 A | 1/1998 | Dinsmore et al. | |
| 5,736,487 A | 4/1998 | Sugai et al. | |
| 5,852,192 A | 12/1998 | Himmelsbach et al. | |
| 6,451,832 B2 | 9/2002 | Ries et al. | |
| 6,593,355 B2 | 7/2003 | Ries et al. | |
| 6,720,424 B1 | 4/2004 | Wada et al. | |
| 6,897,237 B2 | 5/2005 | Hori et al. | |
| 2001/0006977 A1 | 7/2001 | Ries et al. | |
| 2003/0004356 A1 | 1/2003 | Ries et al. | |
| 2003/0158155 A1 | 8/2003 | Hori et al. | |

FOREIGN PATENT DOCUMENTS

| | | |
|---|---|---|
| DE | 2624094 | 5/1975 |
| JP | 2002/193800 | 12/2000 |
| WO | WO96/27583 | 9/1996 |
| WO | WO 03035610 | 10/2001 |
| WO | WO 02/083642 | 10/2002 |

OTHER PUBLICATIONS

Chemical Abstract Service, Jul. 9, 2002, Abstract No. XP002305420.
Database WPI, Section Ch, Week 199951, Aug. 31, 1999, Abstract No. XP002305421.
Database Caplus, Kuragano, Takashi et al., Chemical Abstract Service, May 16, 2002, Abstract No. XP002305419.
Ichikawa, T. et al., Chem. Pharma. Bull., 2001, 49(9), pp. 1110-1119.
Munshi, A.A., Trivedi, J.P., J. Indian Chem. Soc., 1966, 43(4), pp. 277-8.

*Primary Examiner*—Yvonne Eyler
*Assistant Examiner*—MLouisa Lao
(74) *Attorney, Agent, or Firm*—Grace C. Hsu; Mary E McCarthy; Charles M. Kinzig

(57) ABSTRACT

Compounds of formula (I):

$$R^1-Z-Q-N(R^2)-CH_2-X \quad (I)$$

wherein
$R^1$ represents optionally substituted $C_{4-12}$ alkyl, optionally substituted $C_{2-6}$alkylaryl, or optionally substituted 5- or 6-membered aryl or heteroaryl;
Z represents a bond, $CH_2$, O, S, SO, $SO_2$, $NR^4$, $OCR^4R^5$, $CR^4R^5O$, or Z, $R^1$ and Q together form an optionally substituted fused tricyclic group;
Q represents an optionally substituted 5- or 6-membered aryl or heteroaryl ring;
X represents $COR^3$ or $N(OR^8)COR^9$;
$R^2$ represents $SO_2R^{10}$ or $SO_2NR^{10}R^{11}$;
$R^3$ represents $OR^6$, $NR^6R^7$ or $NR^6OH$;
$R^4$ and $R^5$ each independently represents H, $C_{1-6}$ alkyl or $C_{1-6}$alkylaryl;
$R^6$ and $R^7$ each independently represents H, $C_{1-6}$ alkyl, or $C_{1-6}$ alkyl substituted with one or more heteroaryl groups, or $R^6$ and $R^7$ together with the nitrogen atom to which they are attached form a 5- or 6-membered ring which may optionally include 1 or more further heteroatoms selected from O, S and N;
$R^8$ and $R^9$ each independently represents H or $C_{1-6}$ alkyl;
$R^{10}$ and $R^{11}$ each independently represents H or $C_{1-6}$ alkyl; and
and physiologically functional derivatives thereof, with the exception of N-(ethoxycarbonyl)-N-[4-(1H-tetrazol-1-yl)phenyl]glycine, processes for their preparation, pharmaceutical formulations containing them and their use as inhibitors of matrix metalloproteinase enzymes (MMPs) are described.

4 Claims, No Drawings

INHIBITORS OF MATRIX METALLOPROTEINASE

This invention relates to novel chemical compounds, processes for their preparation, pharmaceutical formulations containing them and their use in therapy.

The compounds of the invention are inhibitors of matrix metalloproteinase enzymes (MMPs).

Matrix metalloproteinase enzymes play a major role in extracellular matrix component degradation and remodelling. Examples of MMPs include collagenase 1, 2 and 3, gelatinase A and B, stromelysin 1, 2 and 3, matrilysin, macrophage metalloelastase, enamelysin and membrane type 1, 2, 3 and 4 MMP. The enzymes are secreted by connective tissue cells and inflammatory cells. Enzyme activation can not only initiate tissue damage but induce increased inflammatory cell infiltration into the tissue, leading to more enzyme production and subsequent tissue damage. For example, elastin fragments produced by MMP degradation are believed to stimulate inflammation by attracting macrophages to the site of MMP activity. Inhibition of MMPs provides a means for treating disease states wherein inappropriate metalloprotease activity results in degradation of connective tissue and inflammation.

In one aspect, the present invention provides compounds of formula (I):

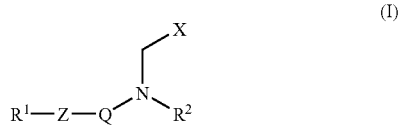

wherein
$R^1$ represents optionally substituted $C_{4-12}$ alkyl, optionally substituted $C_{2-6}$alkylaryl, or optionally substituted 5- or 6-membered aryl or heteroaryl;
Z represents a bond, $CH_2$, O, S, SO, $SO_2$, $NR^4$, $OCR^4R^5$, $CR^4R^5O$, or Z, $R^1$ and Q together form an optionally substituted fused tricyclic group;
Q represents an optionally substituted 5- or 6-membered aryl or heteroaryl ring;
X represents $COR^3$ or $N(OR^8)COR^9$;
$R^2$ represents $SO_2R^{10}$ or $SO_2NR^{10}R^{11}$;
$R^3$ represents $OR^6$, $NR^6R^7$ or $NR^6OH$;
$R^4$ and $R^5$ each independently represents H, $C_{1-6}$ alkyl or $C_{1-4}$ alkylaryl;
$R^6$ and $R^7$ each independently represents H, $C_{1-6}$ alkyl, or $C_{1-6}$ alkyl substituted with one or more heteroaryl groups, or $R^6$ and $R^7$ together with the nitrogen atom to which they are attached form a 5- or 6-membered ring which may optionally include 1 or more further heteroatoms selected from O, S and N;
$R^8$ and $R^9$ each independently represents H or $C_{1-6}$ alkyl;
$R^{10}$ and $R^{11}$ each independently represents H or $C_{1-6}$ alkyl; and and physiologically functional derivatives thereof, with the exception of N-(ethoxycarbonyl)-N-[4-(1H-tetrazol-1-yl)phenyl]glycine.

References to 'aryl' include references to monocyclic carbocyclic aromatic rings (e.g. phenyl) and bicyclic carbocyclic aromatic rings (e.g. naphthyl) and references to 'heteroaryl' include references to mono- and bicyclic heterocyclic aromatic rings containing 1-3 hetero atoms selected from nitrogen, oxygen and sulphur. Examples of monocyclic heterocyclic aromatic rings include e.g. pyridinyl, pyrimidinyl, thiophenyl, furanyl, pyrrolyl, oxazolyl, isoxazolyl, oxadiazolyl, thiazolyl, thiadiazolyl or imidazolyl, and examples of bicyclic heterocyclic aromatic rings include e.g. benzimidazolyl, quinolinyl or indolyl. Carbocyclic and heterocyclic aromatic rings may be optionally substituted, e.g. by one or more $C_{1-6}$ alkyl, $C_{2-6}$ alkenyl, halogen, $(CH_2)_{0-4}OR^6$, $(CH_2)_{0-4}SR^6$, $SO_2R^6$, $COR^6$, aryloxy, thioaryl, cyano, hydroxy, nitro, $NR^6R^7$, —$NR^6COR^7$, —$OCF_3$, —$CF_3$, $COOR^7$, —$OCHCF_2$, —$SCF_3$, —$CONR^6R^7$—$SO_2NR^6R^7$, or like groups.

References to 'alkyl' include references to both straight chain and branched chain aliphatic isomers of the corresponding alkyl. It will be appreciated that references to 'alkylene' and 'alkoxy' shall be interpreted similarly.

Suitably, $R^1$ represents optionally substituted aryl, such as substituted or unsubstituted phenyl.

Suitably, Q represents optionally substituted aryl, such as unsubstituted phenyl.

Suitably $R^2$ represents $SO_2R^{10}$, such as $SO_2C_{1-4}$ alkyl, for example $SO_2CH_3$.

Suitably $R^3$ represents OH or $NR^6R^7$. In particular, X suitably represents $CO_2H$.

Suitably Z represents a bond.

When $R^6$ or $R^7$ represents $C_{1-6}$-alkyl substituted with one or more heteroaryl groups, suitably the $C_{1-6}$ alkyl group will be methyl or ethyl; suitably the alkyl group will be substituted with one heteroaryl group. Suitably, one of $R^6$ or $R^7$ represents H.

One subgroup of compounds of formula (I) is represented by formula (Ia):

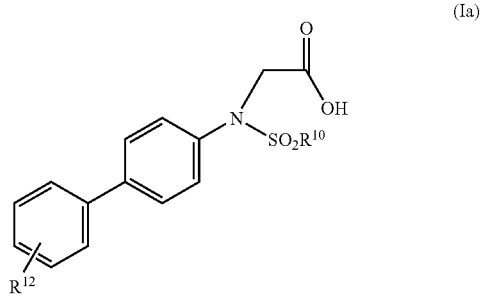

wherein $R^{10}$ represents H or $C_{1-6}$ alkyl, preferably $C_{1-4}$ alkyl, most preferably methyl;
$R^{12}$ represents H, halo, $CF_3$, cyano, $OCF_3$, nitro, $OR^{13}$, $SR^{13}$, $COR^{13}$ or $C_{1-6}$ alkyl, for example, methyl;
$R^{13}$ represents $C_{1-6}$ alkyl or $C_{1-4}$alkylaryl;

and physiologically functional derivatives thereof.

Preferably $R^{12}$ is in the meta or para position. Most preferably $R^{12}$ is in the para position.

A further or alternative subgroup of compounds of formula (I) is represented by formula (Ia) wherein $R^{10}$ represents H or $C_{1-6}$ alkyl, such as $C_{1-4}$ alkyl, for example methyl;
$R^{12}$ represents H, halo, $CF_3$, cyano, $OCF_3$, nitro, $OR^{13}$, $SR^{13}$, or $COR^{13}$;
$R^{13}$ represents H, $C_{1-6}$ alkyl or $C_{1-4}$alkylaryl;

and physiologically functional derivatives thereof.

Preferably $R^{12}$ is in the meta or para position. Most preferably $R^{12}$ is in the para position.

By the term "physiologically functional derivative" is meant a chemical derivative of a compound of formula (I) having the same physiological function as the free compound of formula (I), for example, by being convertible in the body thereto and includes any pharmaceutically acceptable esters, amides and carbamates, salts and solvates of compounds of formula (I) which, upon administration to the recipient, are capable of providing (directly or indirectly) compounds of formula (I) or active metabolite or residue thereof.

Salts of compounds of formula (I) are also provided by the invention. Suitable salts of the compounds of formula (I) include physiologically acceptable salts and salts which may not be physiologically acceptable but may be useful in the preparation of compounds of formula (I) and physiologically acceptable salts thereof. If appropriate, acid addition salts may be derived from inorganic or organic acids, for example hydrochlorides, hydrobromides, sulphates, phosphates, acetates, benzoates, citrates, succinates, lactates, tartrates, fumarates, maleates, 1-hydroxy-2-naphthoates, palmoates, methanesulphonates, formates or trifluoroacetates.

Examples of solvates include hydrates.

When compounds of formula (I) contain chiral centres, the invention extends to mixtures of enantiomers (including racemic mixtures) and diastereoisomers as well as to individual enantiomers. Generally it is preferred to use a compound of formula (I) in the form of a purified single enantiomer.

The compounds of formula (I) and salts and solvates thereof may be prepared by the methodology described hereinafter, constituting a further aspect of this invention.

A first process (A) according to the invention for preparing a compound of formula (I) wherein Z represents a bond and $R^1$ represents an optionally substituted $C_{2-6}$alkylaryl or an optionally substituted 5- or 6-membered aryl or heteroaryl, comprises reacting a compound of formula (II):

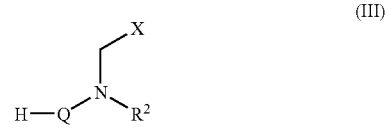

wherein $R^2$, Q and X are as previously defined for formula (I) and L represents a leaving group, with a reagent suitable to introduce the group $R^1$, such as a compound $R^1B(OH)_2$, suitably in the presence of a catalyst, such as a nobel metal catalyst e.g. palladium, and a suitable base, such as an alkali metal carbonate, e.g. caesium carbonate. The reaction is conveniently carried out in a suitable solvent, such as a polar organic solvent, e.g. dimethyl formamide. Suitable leaving groups represented by L include halides, especially bromide or iodide.

For example, for the synthesis of a (optionally substituted) [(1,1'-biphenyl-4-yl)(methyl-sulfonyl)amino]acetic acid according to the invention a phenyl boronic acid may be reacted with [(4-bromophenyl)(methylsulfonyl)amino]acetic acid in the presence of a suitable catalyst:

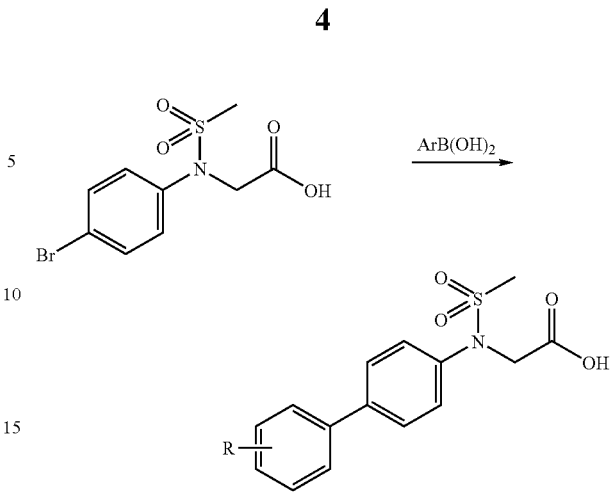

A second process (B) according to the invention for preparing a compound of formula (I) wherein Z represents a bond and $R^1$ represents an optionally substituted $C_{4-12}$alkyl, comprises reacting a compound of formula (III):

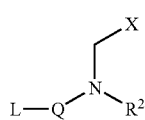

wherein $R^2$, Q and X are as previously defined for formula (I), with a reagent suitable to introduce the group $R^1$, such as a compound $R^1$-L, wherein L is a suitable leaving group, for example halide, suitably in the presence of a catalyst, for example a Lewis acid catalyst such as $AlCl_3$. A Friedel-Crafts reaction may accordingly be appropriate.

A third process (C) according to the invention for preparing a compound of formula (I) wherein Z represents O, S, SO, $SO_2$, $NR^4$ or $OCR^4R^5$, and $R^1$ represents an optionally substituted $C_{4-12}$alkyl comprises reacting a compound of formula (IV):

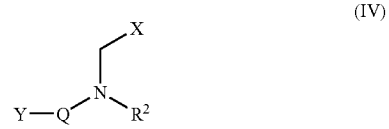

wherein X, $R^2$ and Q are as previously defined for formula (I), and Y represents OH, SH, $NR^4H$ or $HOCR^4R^5$, with a reagent suitable to introduce the group $R^1$, such as a compound $R^1$-L, wherein L is a suitable leaving group. The reaction is conveniently carried out in a suitable solvent, such as an alcohol solvent, e.g. ethanol, under basic conditions, for example in the presence of an aqueous hydroxide such as sodium hydroxide. Suitable leaving groups represented by L include halides, especially bromide or iodide.

For compounds in which Z represents SO or $SO_2$, the compound of formula (I) may conveniently be prepared by initial preparation of the compound in which Z represents S, followed by oxidation of the sulphide to the sulfoxide or the sulfone. The oxidation step may be carried out using methods known in the art such as oxidation with hydrogen peroxide in the case of the sulfone, or oxidation with Oxone® (potassium peroxymonosulfate) in the case of the sulfoxide.

A fourth process (D) according to the invention for preparing a compound of formula (I) wherein Z represents O, S, SO, SO$_2$, or NR$^4$, and R$^1$ represents an optionally substituted C$_{2-6}$alkylaryl or an optionally substituted 5- or 6-membered aryl or heteroaryl, comprises reacting a compound of formula (IV):

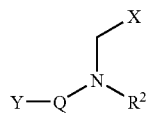

(IV)

wherein X, R$^2$ and Q are as previously defined for formula (I), and Y represents OH, SH or NR$^4$H, with a reagent suitable to introduce the group R$^1$, such as a compound R$^1$-L, wherein L is a suitable leaving group. The reaction is conveniently carried out in a suitable solvent, such as a solvent containing a heteroatom, e.g. pyridine, in the presence of a suitable catalyst, for example palladium catalyst (preferred for Y=NR$^4$H) or a copper catalyst (preferred for Y=OH or SH). Suitable leaving groups represented by L include halides, especially bromide or iodide.

For compounds in which Z represents SO or SO$_2$, the compound of formula (I) may conveniently be prepared by initial preparation of the compound in which Z represents S, followed by oxidation of the sulphide to the sulfoxide or the sulfone. The oxidation step may be carried out using methods known in the art such as oxidation with hydrogen peroxide in the case of the sulfone, or oxidation with Oxone® (potassium peroxymonosulfate) in the case of the sulfoxide.

A fifth process (E) according to the invention for preparing a compound of formula (I) wherein Z represents OCR$^4$R$^5$ and R$^1$ represents an optionally substituted C$_{2-6}$alkylaryl or an optionally substituted 5- or 6-membered aryl or heteroaryl, comprises reacting a compound of formula (V):

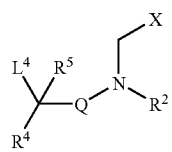

(V)

wherein X, R$^2$ and Q are as previously defined for formula (I) and L$^4$ is a suitable leaving group, with a reagent suitable to introduce the group R$^1$—O such as a compound R$^1$—OH. The reaction is conveniently carried out in a suitable solvent, such as an alcohol solvent, e.g. ethanol, under basic conditions, for example in the presence of an aqueous hydroxide such as sodium hydroxide. Suitable leaving groups represented by L$^4$ include halides, especially bromide or iodide.

A sixth process (F) according to the invention for preparing a compound of formula (I) wherein Z represents CR$^4$R$^{50}$, comprises reacting a compound of formula (IV):

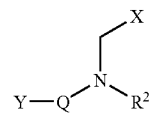

(IV)

wherein X, R$^2$ and Q are as previously defined for formula (I), and Y represents OH, with a reagent suitable to introduce the group R$^1$CR$^4$R$^5$ such as a compound R$^1$CR$^4$R$^5$-L, wherein L is a suitable leaving group. The reaction is conveniently carried out in a suitable solvent, such as an alcohol solvent, e.g. ethanol, under basic conditions, for example in the presence of an aqueous hydroxide such as sodium hydroxide. Suitable leaving groups represented by L include halides, especially bromide or iodide.

A seventh process (G) according to the invention for preparing a compound of formula (I) wherein Z represents CH$_2$, comprises reacting a compound of formula (III):

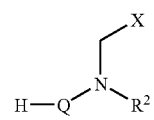

(III)

wherein R$^2$, Q and X are as previously defined for formula (I), with a reagent suitable to introduce the group R$^1$CH$_2$, such as a compound R$^1$CH$_2$-L, wherein L is a suitable leaving group, for example halide, suitably in the presence of a catalyst, for example a Lewis acid catalyst such as AlCl$_3$. A Friedel-Crafts reaction may accordingly be appropriate.

An eighth process (H) according to the invention comprises reacting a compound of formula (VI)

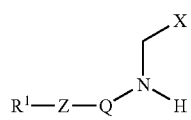

(VI)

or a protected derivative thereof, wherein R$^1$, Z, Q and X are as previously defined for formula (I), with a reagent suitable to introduce the group R$^2$ as previously defined for formula (I). An example of such a reagent is R$^2$-L wherein R$^2$ is as previously defined for formula (I) and L is a suitable leaving group, for example a halide, such as a chloride, in the presence of a base, such as a tertiary amine, for example a trialkyl amine such as triethylamine.

A nineth process (J) according to the invention comprises carrying out a process selected from processes (A) to (H) followed by interconversion of one or more functional groups.

Compounds of formula (II) may be prepared for example by reaction of a compound of formula L-Q-NH—CH$_2$X (formula (VII)) with a compound of formula R$^2$-L$^2$ wherein L, Q, X and R$^2$ are as previously defined for formula (II) and L$^2$ represents a leaving group, in the presence of a base. In turn compounds of formula (VII) may be prepared by reaction of a compound of formula L-Q-NH$_2$ with a compound of formula X—CH$_2$L$^3$ wherein L, Q and X are as previously defined and L$^3$ represents a leaving group. The reaction is preferably carried out in a polar organic solvent (for example dimethyl formamide) in the presence of a base (for example potassium carbonate).

Compounds of formula (III) may be prepared in an analogous fashion to compounds of formula (II) starting from a compound of formula H-Q-NH—CH$_2$X (formula (VIII)) in place of a compound of formula (VII). In turn compounds of formula (VIII) may be prepared by reaction of a compound of formula H-Q-NH$_2$ with a compound of formula X—CH$_2$L$^3$ wherein Q and X are as previously defined and L$^3$ represents a leaving group. The reaction is preferably carried out in a polar organic solvent (for example dimethyl formamide) in the presence of a base (for example potassium carbonate).

Similarly, compounds of formula (IV) may be prepared in an analogous fashion to the compounds of formula (II) starting from a compound of formula Y-Q-NH—CH$_2$X (formula (IX)) wherein Y represents OH, SH, NR$^4$H or HCR$^4$R$^5$, in place of a compound of formula (VII). In turn compounds of formula (IX) may be prepared by reaction of a compound of formula Y-Q-NH$_2$ with a compound of formula X—CH$_2$L$^3$ wherein Y, Q and X are as previously defined and L$^3$ represents a leaving group. The reaction is preferably carried out in a polar organic solvent (for example dimethyl formamide) in the presence of a base (for example potassium carbonate).

Similarly, compounds of formula (V) may be prepared in an analogous fashion to the compounds of formula (II) starting from a compound of formula L$^4$CR$^4$R$^5$-Q-NH—CH$_2$X (formula (X)) in place of a compound of formula (VII). In turn compounds of formula (X) may be prepared by reaction of a compound of formula L$^4$CR$^4$R$^5$-Q-NH$_2$ with a compound of formula X—CH$_2$L$^3$ wherein L$^4$, Q and X are as previously defined and L$^3$ represents a leaving group. The reaction is preferably carried out in a polar organic solvent (for example dimethyl formamide) in the presence of a base (for example potassium carbonate).

Compounds of formula (VI) may be prepared from compounds of formula R$^1$ZQNH$_2$ (formula (XI)) wherein R$^1$, Z and Q are as previously defined for formula (I), by reaction with a reagent suitable to introduce the group CH$_2$X, wherein X is as previously defined for formula (I). An example of such a reagent is L-CH$_2$X, wherein X is as previously defined for formula (I) and L is a suitable leaving group, for example a halide, such as a bromide, in the presence of a base (for example potassium carbonate). Compounds of formula (XI) may be prepared by conventional methods well known to those skilled in the art, for example, by reduction of a compound of formula R$^1$ZQNO$_2$.

Compounds of formula R$^2$-L$^2$, L-Q-NH$_2$, X—CH$_2$L$^3$, H-Q-NH$_2$, Y-Q-NH$_2$, and L$^4$CR$^4$R$^5$-Q-NH$_2$ are known or may be prepared by known methods.

Depending on the identity of the group X, it may be preferable for that group to be protected during the steps of the synthesis of a compound of formula (II). Suitable protecting groups are known to those skilled in the art. Protecting groups may be any conventional protecting groups, for example as described in "Protective Groups in Organic Synthesis" by Theodora Greene and Peter G. M. Wuts (John Wiley and Sons Inc. 1999). Suitable carboxylic acid protecting groups include but are not limited to carboxylic acid esters, for example, methyl ester, ethyl ester, t-butyl ester, aryl esters e.g. benzyl ester.

For example, a compound of formula (II) in which X is COR$^3$, R$^3$ is OH, R$^2$ is SO$_2$Me, Q is phenyl and L is 4-bromo may be prepared by the following scheme in which the free acid group of the final product is protected as the t-butyl ester during the synthesis substitution reactions:

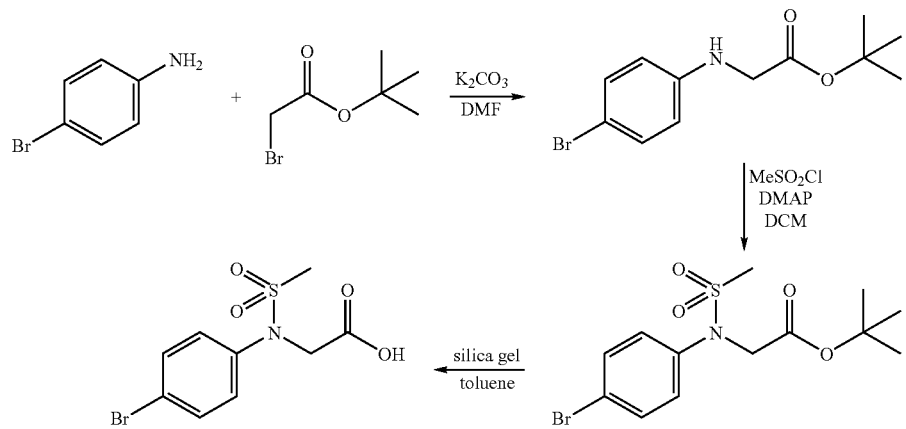

It will be appreciated by those skilled in the art that compounds of formula (I) may also be prepared from other compounds of formula (I) by interconversion using processes such as oxidation, reduction, substitution, deprotection etc., standard in the art of synthetic chemistry.

The enantiomeric compounds of the invention may be obtained (a) by the separation of the components of the corresponding racemic mixture, for example, by chiral chromatography, enzymatic resolution methods or preparing and separating suitable diastereoisomers, (b) by direct synthesis from the appropriate chiral starting materials by the methods described above, or (c) by methods analogous to those described above using chiral reagents.

Optional conversion of a compound of formula (I) to a corresponding salt may conveniently be effected by reaction with the appropriate acid or base. Optional conversion of a compound of formula (I) to a corresponding solvate or other physiologically functional derivative may be effected by methods known to those skilled in the art.

Compounds of formula (I) may be useful for the treatment of any conditions in which inhibition of matrix metalloproteinase would be beneficial, especially in the treatment of inflammatory diseases and autoimmune disorders.

Examples of inflammatory conditions and autoimmune disorders in which the compounds of the invention have potentially beneficial effects include diseases of the respiratory tract such as asthma (including allergen-induced asthmatic reactions), cystic fibrosis, bronchitis (including chronic bronchitis), chronic obstructive pulmonary disease (COPD), adult respiratory distress syndrome (ARDS), chronic pulmonary inflammation, rhinitis and upper respiratory tract inflammatory disorders (URID), ventilator induced lung injury, silicosis, pulmonary sarcoidosis, idiopathic pulmonary fibrosis, bronchopulmonary dysplasia, arthritis, e.g. rheumatoid arthritis, osteoarthritis, infectious arthritis, psoriatic arthritis, traumatic arthritis, rubella arthritis, Reiter's syndrome, gouty arthritis and prosthetic joint failure, gout, acute synovitis, spondylitis and non-articular inflammatory conditions, e.g. herniated/ruptured/prolapsed intervertebral disk syndrome, bursitis, tendonitis, tenosynovitic, fibromyalgic syndrome and other inflammatory conditions associated with ligamentous sprain and regional musculoskeletal strain, inflammatory disorders of the gastrointestinal tract, e.g. ulcerative colitis, diverticulitis, Crohn's disease, inflammatory bowel diseases, irritable bowel syndrome and gastritis, multiple sclerosis, systemic lupus erythematosus, scleroderma, autoimmune exocrinopathy, autoimmune encephalomyelitis, diabetes, tumor angiogenesis and metastasis, cancer including carcinoma of the breast, colon, rectum, lung, kidney, ovary, stomach, uterus, pancreas, liver, oral, laryngeal and prostate, melanoma, acute and chronic leukemia, periodontal disease, neurodegenerative disease, Alzheimer's disease, Parkinson's disease, epilepsy, muscle degeneration, inguinal hernia, retinal degeneration, diabetic retinopathy, macular degeneration, ocular inflammation, bone resorption diseases, osteoporosis, osteopetrosis, graft vs. host reaction, allograft rejections, sepsis, endotoxemia, toxic shock syndrome, tuberculosis, usual interstitial and cryptogenic organizing pneumonia, bacterial meningitis, systemic cachexia, cachexia secondary to infection or malignancy, cachexia secondary to acquired immune deficiency syndrome (AIDS), malaria, leprosy, leishmaniasis, Lyme disease, glomerulonephritis, glomerulosclerosis, renal fibrosis, liver fibrosis, pancreatitis, hepatitis, endometriosis, pain, e.g. that associated with inflammation and/or trauma, inflammatory diseases of the skin, e.g. dermatitis, dermatosis, skin ulcers, psoriasis, eczema, systemic vasculitis, vascular dementia, thrombosis, atherosclerosis, restenosis, reperfusion injury, plaque calcification, myocarditis, aneurysm, stroke, pulmonary hypertension, left ventricular remodeling and heart failure.

Diseases of principal interest include COPD and inflammatory diseases of the respiratory tract and joints and vascular diseases.

It will be appreciated by those skilled in the art that reference herein to treatment extends to prophylaxis as well as the treatment of established conditions.

There is thus provided as a further aspect of the invention a compound of formula (I) or a physiologically acceptable derivative thereof for use in medicine.

According to another aspect of the invention, there is provided the use of a compound of formula (I) or a physiologically acceptable derivative thereof for the manufacture of a medicament for the treatment of inflammatory conditions or autoimmune disorders.

In a further or alternative aspect there is provided a method for the treatment of a human or animal subject suffering from or susceptible to an autoimmune disorder or an inflammatory condition which method comprises administering to said human or animal subject an effective amount of a compound of formula (I) or a physiologically functional derivative thereof.

The compounds according to the invention may be formulated for administration in any convenient way, and the invention therefore also includes within its scope pharmaceutical compositions comprising a compound of formula (I) or a physiologically acceptable derivative thereof together, if desirable, with one or more physiologically acceptable diluents or carriers.

There is also provided a process for preparing such a pharmaceutical formulation which comprises mixing the ingredients.

The compounds according to the invention may, for example, be formulated for oral, inhaled, intranasal, topical, buccal, parenteral or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

Compounds according to the invention for topical administration may be formulated as creams, gels, ointments or lotions or as a transdermal patch. Such compositions may for example be formulated with an aqueous or oily base with the addition of suitable thickening, gelling, emulsifying, stabilising, dispersing, suspending, and/or colouring agents.

Lotions may be formulated with an aqueous or oily base and will in general also contain one or more emulsifying agents, stabilising agents, dispersing agents, suspending agents, thickening agents, or colouring agents. They may also contain a preservative.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

The pharmaceutical compositions according to the invention may also be used in combination with other therapeutic agents, for example anti-inflammatory agents (such as corticosteroids (e.g. fluticasone propionate, beclomethasone dipropionate, mometasone furoate, triamcinolone acetonide or budesonide) or NSAIDs (e.g. sodium cromoglycate, nedocromil sodium, PDE-4 inhibitors, leukotriene antagonists, CCR-3 antagonists, iNOS inhibitors, tryptase and elastase inhibitors, beta-2 integrin antagonists and adenosine 2a agonists)) or beta adrenergic agents (such as salmeterol, salbutamol, formoterol, fenoterol or terbutaline and salts thereof) or antiinfective agents (e.g. antibiotics, antivirals).

It will be appreciated that when the compounds of the present invention are administered in combination with other therapeutic agents normally administered by the inhaled or intranasal route, that the resultant pharmaceutical composition may be administered by the inhaled or intranasal route.

Compounds of the invention may conveniently be administered in amounts of, for example, 0.01 to 100 mg/kg body weight, preferably 0.1 to 25 mg/kg body weight, more preferably 0.3 to 5 mg/kg body weight. The compounds may be given more than once daily to be equivalent to the total daily dose. The precise dose will of course depend on the age and condition of the patient and the particular route of administration chosen and will ultimately be at the discretion of the attendant physician.

No toxicological effects are expected when a compound according to the present invention is administered in the above mentioned dose range.

Compounds of the invention may be tested for in vitro activity in accordance with the following assay:

The fluorescent peptide substrate used in the MMP-12 assay is FAM-Gly-Pro-Leu-Gly-Leu-Phe-Ala-Arg-Lys (TAMRA), where FAM represents carboxyfluorescein, and TAMRA represents tetramethylrhodamine. MMP12 catalytic domain (residues 106-268) protein was expressed in *E. coli* in the form of insoluble inclusion bodies & stored in concentrated solution under denaturing conditions (8M guanidine hydrochloride). Enzyme was refolded into active form in situ by direct dilution into assay reactions. The 51 uL reactions are run in NUNC-brand black, square 384-well plates, each well containing 2 uM substrate, 20 nM enzyme, and 0.001-100 uM inhibitor, in 50 mM HEPES, pH 7.5, 150 mM NaCl, 10 mM CaCl2, 1 uM ZnAc, 0.6 mM CHAPS, and 2% DMSO. Postitive control wells contain no inhibitor. Negative control wells are effected by either pre-dispensing the EDTA quench (see below) or by omiting enyme. Reactions are incubated at ambient temperature for 120 min, then quenched by the addition of 15 uL of 100 mM EDTA. Product formation in each well is quantified by measuring flourescense with a Molecular Devices Acquest. The excitation wavelength is set at 485 nM, and the emmision wavelenght is 530 nM. $IC_{50}$ values were obtained by first calculating the percent inhibition (% I) at each inhibitor concentration (% I=100*(1−(I−C2)/(C1−C2)), where C1 is the mean of the positive controls, and C2 is the mean of the negative controls), then fitting the % I vs. inhibitor concentration [I] data to: % I=A+((B−A)/(1+((C/[I]^D))), where A is the lower asymptote, B is the upper asymptote, C is the IC50 value, and D is the slope factor. When tested in this assay, compounds of Examples 1 to 11 had IC50s below 100 micromolar.

The invention may be illustrated by reference to the following examples, which should not be construed as a limitation thereto:

EXAMPLES

General Experimental Details
LC/MS data were obtained under the following conditions:
Column: 3.3 cm×4.6 mm ID, 3 um ABZ+PLUS
Flow Rate: 3 ml/min
Injection Volume: 5 μl
Temp: RT
UV Detection Range: 215 to 330 nm
Solvents: A: 0.1% Formic Acid+10 mMolar Ammonium Acetate.
B: 95% Acetonitrile+0.05% Formic Acid

| Gradient: | | |
|---|---|---|
| Time | A % | B % |
| 0.00 | 100 | 0 |
| 0.70 | 100 | 0 |
| 4.20 | 0 | 100 |
| 5.30 | 0 | 100 |
| 5.50 | 100 | 0 |

$^1$HNMR spectra were obtained at 400 MHz on a Bruker-Spectrospin Ultrashield 400 spectrophotometer.

All synthesis starting materials and reagents were used as obtained from commercial suppliers.

Example 1

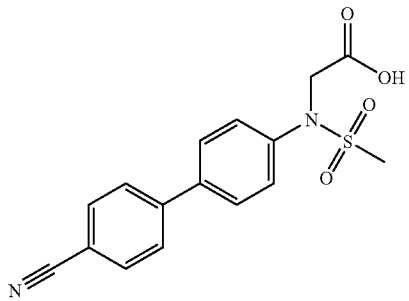

[(4'-Cyano-1,1'-biphenyl-4-yl)(methylsulfonyl)amino]acetic acid

A solution of [(4-bromophenyl)(methylsulfonyl)amino] acetic acid (intermediate 3, 20 mg, 65 μmol) in dimethoxyethane (1 mL) was added in one portion to a mixture of 4-cyanophenyl-boronic acid (9.5 mg, 65 μmol) and fibrecat FC1001 (2.71% Pd; 25 mg, 6.5 μmol) in a Smith microwave reaction vial. Aqueous sodium carbonate solution (1.0 M; 130 μL, 130 μmol) was added and the vial capped. The crude reaction mixture was heated at 150° C. for 15 min using a Smith Synthesiser microwave reactor. On cooling the vial was opened and the contents were filtered through a Whatman 5 μM filter tube, washing the filter cake with methanol (2×1 mL). The filtrate was evaporated and the resulting residue was purified using mass directed auto-preparative reverse phase HPLC to give the title compound (1.1 mg, 5%) as a white solid. LC/MS: 2.94 min; z/e 329, calcd (M−1) 329. $^1$H NMR (400 MHz: MeOD): 7.80 (4H), 7.75 (2H), 7.65 (2H), 4.45 (2H), 3.10 (3H).

Example 2

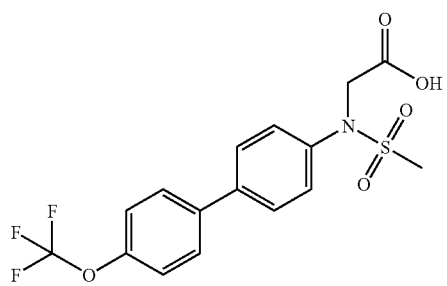

{(Methylsulfonyl)[4'-(trifluoromethoxy)-1,1'-biphenyl-4-yl]amino}acetic acid

Prepared analogously to Example 1. LC/MS: 3.41 min; z/e 407, calcd (M+18) 407.

Example 3

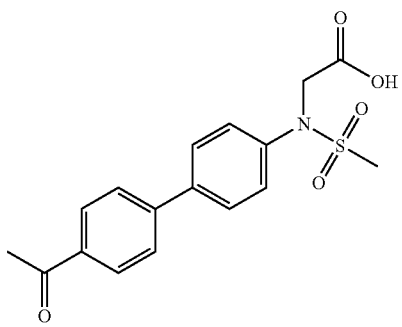

[(4'-Acetyl-1,1'-biphenyl-4-yl)(methylsulfonyl)amino]acetic acid

Prepared analogously to Example 1. LC/MS: 2.98 min; z/e 365, calcd (M+18) 365.

Example 4

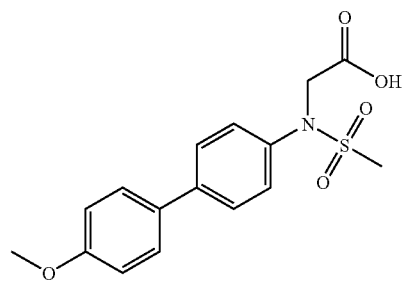

[(4'-Methoxy-1,1'-biphenyl-4-yl)(methylsulfonyl)amino]acetic acid

Prepared analogously to Example 1. LC/MS: 3.17 min; z/e 353, calcd (M+18) 353.

Example 5

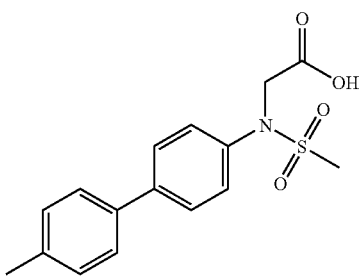

[(4'-Methyl-1,1'-biphenyl-4-yl)(methylsulfonyl)amino]acetic acid

Prepared analogously to Example 1. LC/MS: 3.24 min; z/e 337, calcd (M+18) 337.

Example 6

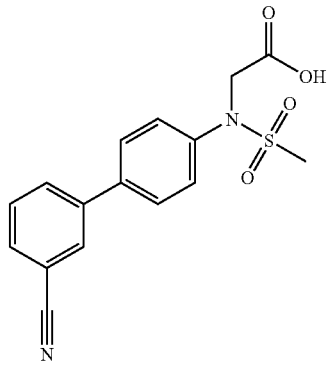

[(3'-Cyano-1,1'-biphenyl-4-yl)(methylsulfonyl)amino]acetic acid

Prepared analogously to Example 1. LC/MS: 3.05 min; z/e 348, calcd (M+18) 348.

Example 7

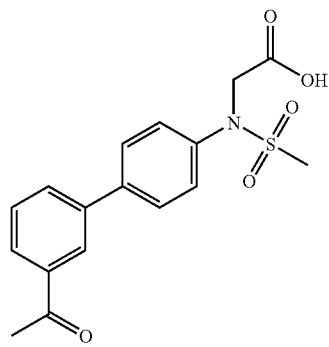

[(3'-Acetyl-1,1'-biphenyl-4-yl)(methylsulfonyl)amino]acetic acid

Prepared analogously to Example 1. LC/MS: 2.82 min; z/e 365, calcd (M+18) 365.

Example 8

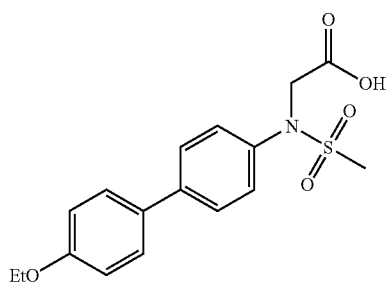

[(4'-Ethoxy-1,1'-biphenyl-4-yl)(methylsulfonyl)amino]acetic acid

Prepared analogously to Example 1. LC/MS: 3.24 min; z/e 367, calcd (M+18) 367.

Example 9

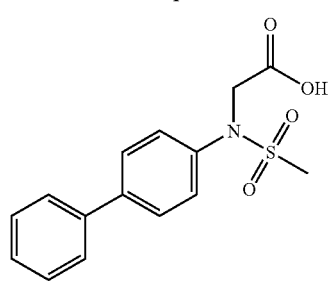

[(1,1'-Biphenyl-4-yl)(methylsulfonyl)amino]acetic acid

Prepared analogously to Example 1. LC/MS: 3.04 min; z/e 323, calcd (M+18) 323.

Example 10

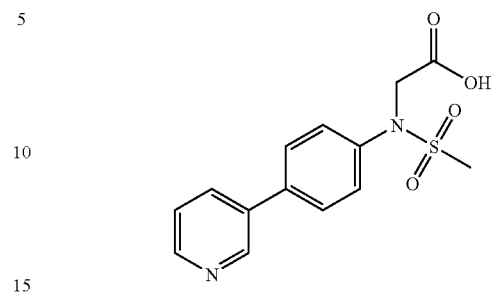

[(pyridin-3-ylphenyl-4-yl)(methylsulfonyl)amino] acetic acid (i.e. N-(methylsulfonyl)-N-(4-pyridin-3-ylphenyl)glycine)

Prepared analogously to Example 1. LC/MS: 1.86 min; z/e 307, calcd (M+1) 307.

Example 11

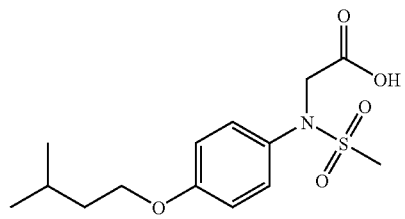

N-{4-[(3-Methylbutyl)oxy]phenyl}-N-(methylsulfonyl)glycine

Trifluoroacetic acid (2.5 mL) was added in one portion to a stirred solution of 1,1-dimethylethyl N-{4-[(3-methylbutyl)oxy]phenyl}-N-(methylsulfonyl)glycinate (intermediate 7, 140 mg, 0.378 mmol) in dichloromethane (5 mL) at room temperature under an atmosphere of nitrogen. The resulting mixture was stirred for 3 h then the volatiles evaporated. A portion of the crude orange product was purified by reverse phase mass directed preparative HPLC to give the title compound as a white solid (20 mg). LC/MS: 3.22 min; z/e 333, calcd (M+18) 333. $^1$H NMR (400 MHz; MeOD): 0.95 (6H), 1.75 (2H), 1.85 (1H), 3.05 (3H), 4.05 (2H), 4.35 (2H), 6.90 (2H), 7.40 (2H).

Intermediate 1

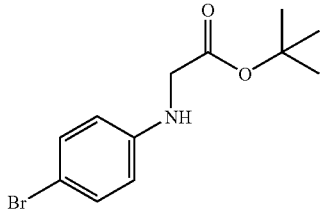

tert-Butyl [(4-bromophenyl)amino]acetate t-Butylbromoacetate (6.24 g, 4.72 mL, 32.0 mmol) was added in one portion to a stirred suspension of 4-bromonaniline (5.00 g, 29.1 mmol) and potassium carbonate (4.02 g, 29.1 mmol) in dimethylformamide (100 mL) at room temperature under nitrogen. The resulting mixture was stirred for 14 h then the volatiles were evaporated. The residue was partitioned between dichloromethane (50 mL) and water (50 mL). The aqueous phase was extracted with dichloromethane (3×50 mL) then the organic extracts were combined, dried (magnesium sulfate) and the solvent evaporated. The residue was chromatographed on silica gel (20% ethyl acetate:cyclohexane) to give the title compound as a white solid (5.86 g, 70%). LC/MS: 3.65 min; z/e 286 and 288, calcd (M+1) 286 and 288. $^1$H NMR (400 MHz: CDCl$_3$): 7.30 (2H), 6.50 (2H), 4.35 (1H), 3.75 (2H), 1.45 (9H).

Intermediate 2

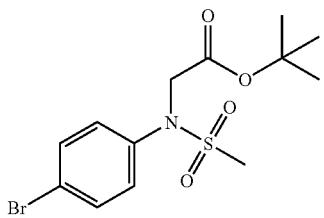

tert-Butyl [(4-bromophenyl)(methylsulfonyl)amino]acetate

A solution of tert-butyl [(4-bromophenyl)amino]acetate (intermediate 1, 5.86 g, 20.5 mmol), methanesulfonyl chloride (2.58 g, 1.74 mL, 22.5 mmol), triethylamine (4.15 g, 5.71 mL, 41.0 mmol) and 4-dimethylaminopyridine (260 mg, 2.05 mmol) in dichloromethane (100 mL) was heated at reflux for 14 h. A second portion of methanesulfonyl chloride (2.58 g, 1.74 mmol, 22.5 mmol) was added and heating at reflux continued for a further 48 h. The reaction was cooled to room temperature and extracted with aqueous hydrochloric acid solution (1.0 M; 3×50 mL). The organic phase was dried (magnesium sulfate) and evaporated to dryness. The residue was chromatographed on silica gel (10% diethyl ether:cyclohexane) to give the title compound as a pale cream solid (2.37 g, 32%). LC/MS: 3.35 min; z/e 381 and 383, calcd (M+18) 381 and 383. $^1$H NMR (400 MHz: CDCl$_3$): 7.55 (2H), 7.35 (2H), 4.30 (2H), 3.10 (3H), 1.45 (9H).

Intermediate 3

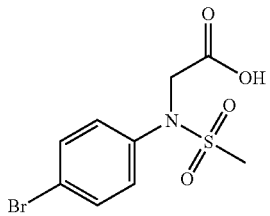

[(4-Bromophenyl)(methylsulfonyl)amino]acetic acid

A suspension of tert-butyl [(4-bromophenyl)(methylsulfonyl) amino]acetate (intermediate 2, 1.00 g, 2.74 mmol) and silica gel (13.7 g) in toluene (88 mL) was heated at reflux for 4 h. The reaction was cooled to room temperature and filtered, the filter cake was washed with methanol/dichloromethane (20/80; 2×100 mL). Evaporation of the combined organic filtrates gave the title compound as a white solid (0.81 g, 95%). LC/MS: 2.81 min; z/e 325 and 327, calcd (M+18) 325 and 327. $^1$H NMR (400 MHz: MeOD): 7.45 (2H), 7.35 (2H), 4.45 (2H), 3.05 (3H).

Intermediate 4

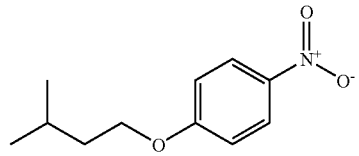

1-[(3-Methylbutyl)oxy]-4-nitrobenzene

1-Bromo-3-methylbutane (7.07 g, 5.60 mL, 46.8 mmol) was added in one portion to a stirred suspension of 4-nitrophenol (5.00 g, 35.9 mmol) and potassium carbonate (5.46 g, 49.5 mmol) in dimethylformamide (50 mL) at room temperature under a nitrogen atmosphere. The resulting mixture was stirred at room temperature for 16 h then the volatiles were evaporated. The residue was partitioned between diethyl ether (50 mL) and water (50 mL) and the phases separated. The aqueous phase was extracted with ether (2×50 mL) then the organic extracts were combined and dried (magnesium sulfate). The solvent was evaporated and the residue chromatographed on silica gel (10% diethyl ether:cyclohexane) to give the title compound as a pale yellow oil (6.63 g, 88%). LC/MS: 3.69 min. $^1$H NMR (400 MHz; CDCl$_3$): 0.95 (6H), 1.75 (2H), 1.85 (1H), 4.05 (2H), 6.95 (2H), 8.20 (2H).

Intermediate 5

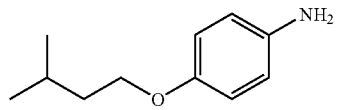

{4-[(3-Methylbutyl)oxy]phenyl}amine

5% Palladium on charcoal (100 mg) was added in one portion to a stirred solution of 1-[(3-methylbutyl)oxy]4-nitrobenzene (intermediate 4, 2.00 g, 9.56 mmol) in ethyl acetate (40 mL) at room temperature under a nitrogen atmosphere. The nitrogen was replaced with hydrogen and stirring was continued for 4 h. The hydrogen was replaced with nitrogen then the crude reaction mixture was filtered through a plug of celite. The solute was evaporated to dryness to give the title compound as a colourless oil (1.71 g, 100%) which was used without purification. LC/MS: 2.29 min; z/e 180, calcd (M+1) 180. ¹H NMR (400 MHz; CDCl₃): 0.95 (6H), 1.65 (2H), 1.85 (1H), 3.10 (2H), 3.90 (2H), 6.65 (2H), 6.75 (2H).

Intermediate 6

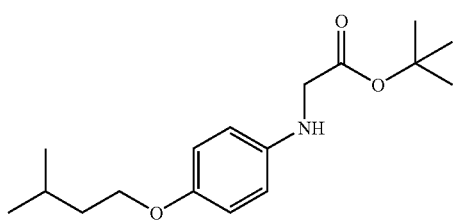

1,1-Dimethylethyl N-{4-[(3-methylbutyl)oxy]phenyl}glycinate t-Butylbromoacetate (1.12 g, 0.85 mL, 5.76 mmol) was added drop wise over 5 min to a stirred suspension of {4-[(3-methylbutyl)oxy]phenyl}amine (intermediate 5, 0.85 g, 4.8 mmol) and potassium carbonate (0.66 g, 4.8 mmol) in dimethylformamide (23.4 mL) at room temperature under a nitrogen atmosphere. After stirring for 14 h the volatiles were evaporated and the residue partitioned between dichloromethane (50 mL) and water (50 mL). The phases were separated and the aqueous phase washed with dichloromethane (2×50 mL). The organic phases were combined, dried (magnesium sulfate) then the solvent evaporated. The residue was chromatographed on silica gel (10% diethyl ether:cyclohexane) to give the title compound (inseparable 10:1 mixture of mono- to di-substitution) as a colourless oil (1.38 g). Mono-product: LC/MS: 3.77 min; z/e 294, calcd (M+1) 294. ¹H NMR (400 MHz; CDCl₃): 0.90 (6H), 1.45 (9H), 1.65 (2H), 1.85 (1H), 3.75 (2H), 3.90 (2H), 6.55 (2H), 6.80 (2H).

Intermediate 7

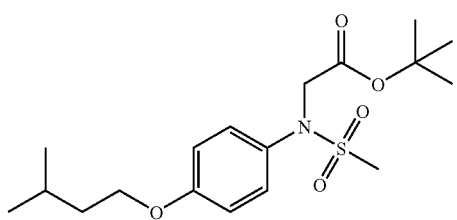

1,1-Dimethylethyl N-{4-[(3-methylbutyl)oxy]phenyl}-N-(methylsulfonyl)glycinate

Methanesulfonylchloride (93 mg, 63 µL, 0.82 mmol) was added in one portion to a stirred solution of 1,1-dimethyl-ethyl N-{4-[(3-methylbutyl)oxy]phenyl}glycinate (intermediate 6, 0.20 g, 0.68 mmol) and triethylamine (138 mg, 189 µL, 1.36 mmol) in dichloromethane (2 mL) at room temperature under a nitrogen atmosphere. Stirring was continued for 3 h then aqueous hydrochloric acid (1.0 M; 2 mL) was added. The organic phase was separated and the aqueous phase washed with dichloromethane (3×5 mL). The organic phases were combined, dried (magnesium sulfate) then evaporated to dryness. The residue was chromatographed on silica gel (30% diethyl ether:cyclohexane) to give the title compound as a white solid (140 mg, 56%). LC/MS: 3.72 min; z/e 389, calcd (M+18) 389. ¹H NMR (400 MHz; CDCl₃): 0.95 (6H), 1.45 (9H), 1.70 (2H), 1.85 (1H), 3.10 (3H), 3.95 (2H), 4.30 (2H), 6.85 (2H), 7.35 (2H).

What is claimed is:

1. A compound of formula (Ia):

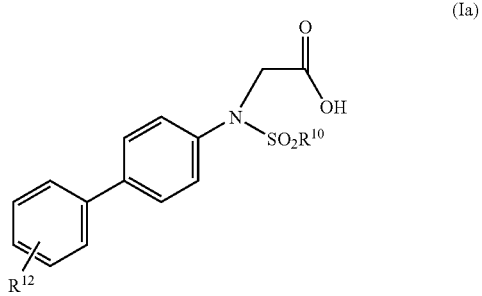

wherein:

$R^{10}$ represents H or $C_{1-6}$ alkyl;

$R^{12}$ represents H, halo, $CF_3$, cyano, $OCF_3$, nitro, $OR^{13}$, $SR^{13}$, $COR^{13}$ or $C_{1-6}$ alkyl;

$R^{13}$ represents $C_{1-6}$ alkyl or $C_{1-4}$alkylaryl;

and physiologically functional derivatives thereof.

2. A pharmaceutical composition comprising a compound of claim 1, and pharmaceutically acceptable carriers or diluents.

3. A process for preparation of compounds of formula (Ia) of claim 1, which comprises:

(A) reacting a compound of formula (II):

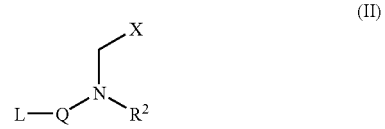

wherein:

$R^2$ is $SO_2R^{10}$, wherein $R^{10}$ is as defined in claim 2;

Q is phenyl; and

X is $CO_2H$; and

L represents a leaving group, with a reagent suitable to introduce phenyl optionally substituted by $R^{12}$, wherein $R^{12}$ is as defined in claim 2;

(H) reacting a compound of formula (VI)

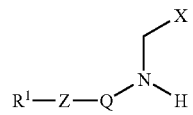

or a protected derivative thereof, wherein:
R$^1$ is phenyl optionally substituted by R$^{12}$, wherein R$^{12}$ us as defined in claim 2,
Z is a bond,
Q is phenyl and
X is CO$_2$H
with a reagent suitable to introduce the group SO$_2$R$^{10}$, wherein R$^{10}$ is as defined in claim 2; or
(J) carrying out a process selected from processes (A) to (H) followed by interconversion of one or more functional groups.

4. The pharmaceutical composition according to claim 2 further comprising one or more therapeutic agents, selected from anti-inflammatory agents, NSAIDs, beta adrenergic agents and anti-infective agents, wherein:
  the anti-inflammatory agents are selected from corticosteroids selected from fluticasone propionate, beclomethasone dipropionate, mometasone furoate, triamcinolone acetonide or budesonide);
  the NSAIDs are selected from sodium cromoglycate, nedocromil sodium, PDE-4 inhibitors, leukotriene antagonists, CCR-3 antagonists, iNOS inhibitors, tryptase and elastase inhibitors, beta-2 integrin antagonists and adenosine 2a agonists;
  the beta adrenergic agents are selected from salmeterol, salbutamol, formoterol, fenoterol or terbutaline and salts thereof; or
  the anti-infective agents are selected from antibiotics or antivirals.

* * * * *